United States Patent [19]

Sullivan

[11] Patent Number: 4,950,238
[45] Date of Patent: Aug. 21, 1990

[54] HYDRO-ROTARY VASCULAR CATHETER
[75] Inventor: Dennis E. Sullivan, Phoenix, Ariz.
[73] Assignee: Clarence E. Sikes, Glendale, Ariz. ; a part interest
[21] Appl. No.: 383,362
[22] Filed: Jul. 20, 1989

Related U.S. Application Data
[63] Continuation-in-part of Ser. No. 216,095, Jul. 7, 1988, abandoned.
[51] Int. Cl.[5] ............................................. A61M 29/00
[52] U.S. Cl. ...................................... 604/22; 606/159; 604/101; 134/167 C
[58] Field of Search ................... 604/22; 606/159, 167, 606/170, 194, 127, 128, 180; 134/167 C, 168 C; 239/214.15

[56] References Cited
U.S. PATENT DOCUMENTS

| | | | |
|---|---|---|---|
| 3,120,346 | 2/1964 | Willhoit | 239/214.15 |
| 4,445,509 | 5/1984 | Auth | 606/159 |
| 4,631,052 | 12/1986 | Kensey | 604/22 |
| 4,715,538 | 12/1987 | Lingnau | 134/167 C |
| 4,749,376 | 6/1988 | Kensey et al. | 604/22 |
| 4,784,636 | 11/1988 | Rydell | 604/22 |
| 4,795,438 | 1/1989 | Kensey et al. | 606/159 |

FOREIGN PATENT DOCUMENTS
3421390 12/1985 Fed. Rep. of Germany ...... 606/159

Primary Examiner—Michael H. Thaler
Assistant Examiner—William Lewis
Attorney, Agent, or Firm—Edward W. Hughes

[57] ABSTRACT

A hydro-rotary vascular catheter for insertion in a body vessel comprises a tubular outer shell having a fluid-directing head rotatably mounted at its distal end. A plurality of outlet passages are formed about the circumference of the fluid-directing head, including a row of primary outlet passages formed near the base of the fluid-directing head and a row of secondary outlet passages formed forwardly of the primary outlet passages. The primary outlet passages are inclined radially and tangentially with respect to the shell to impart a tangential component of velocity to fluid exiting through the primary openings, while the secondary outlet openings are inclined axially in order to eject fluid in a primarily forward direction. A protective shield surrounds the primary openings to prevent the radially ejected fluid from rupturing the walls of the vessel, and to increase the turbulence of the exiting fluid.

12 Claims, 2 Drawing Sheets

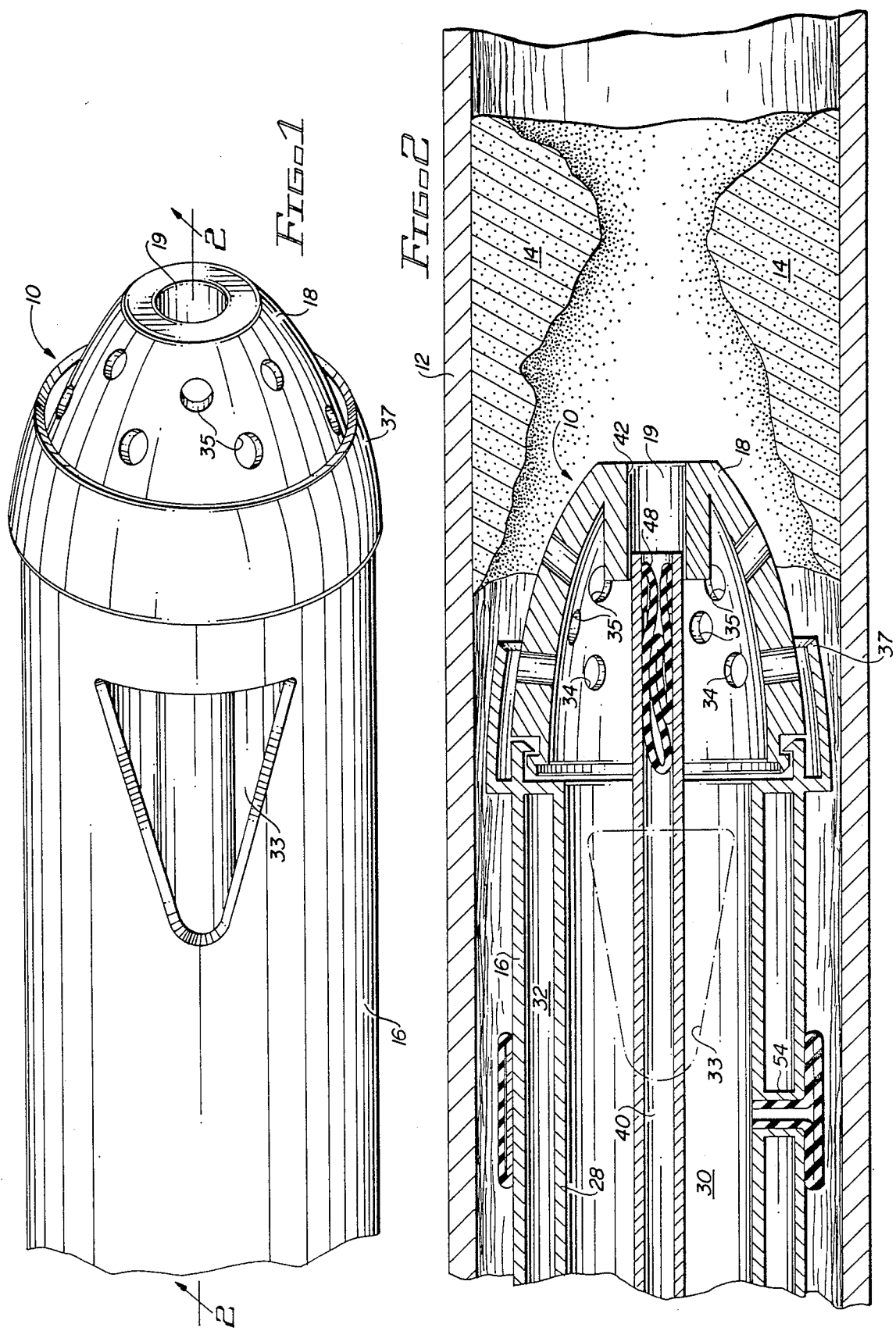

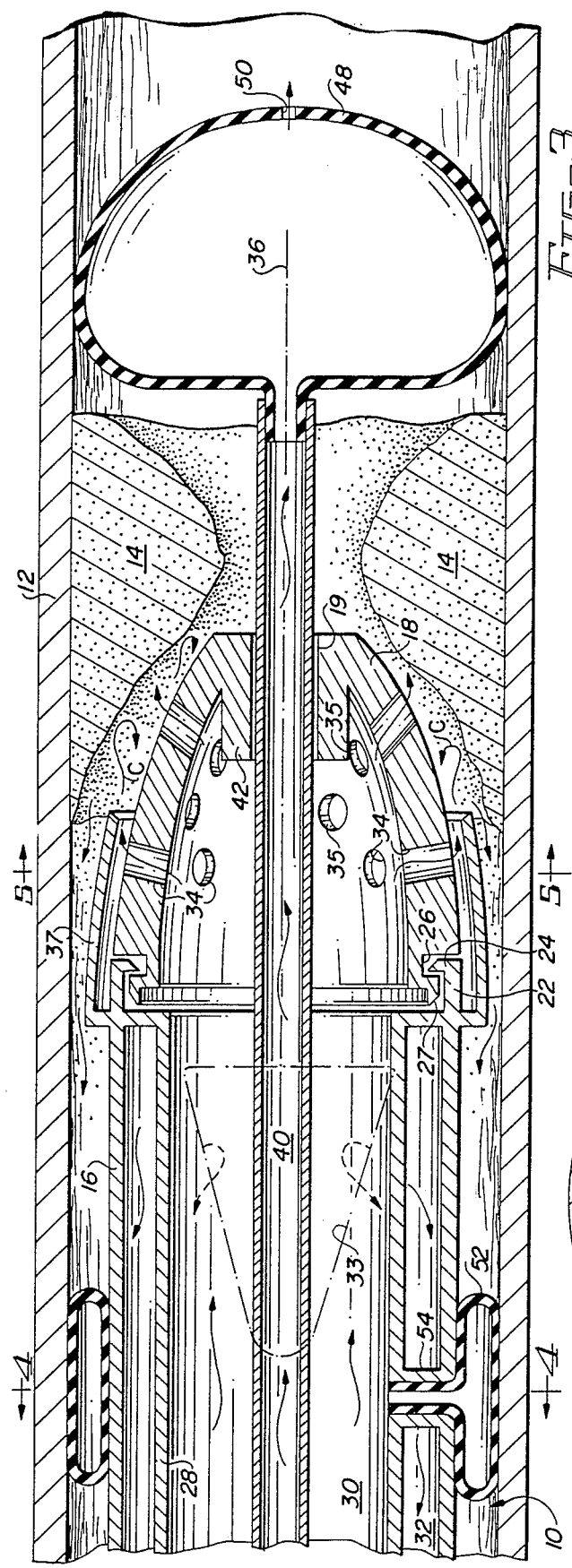
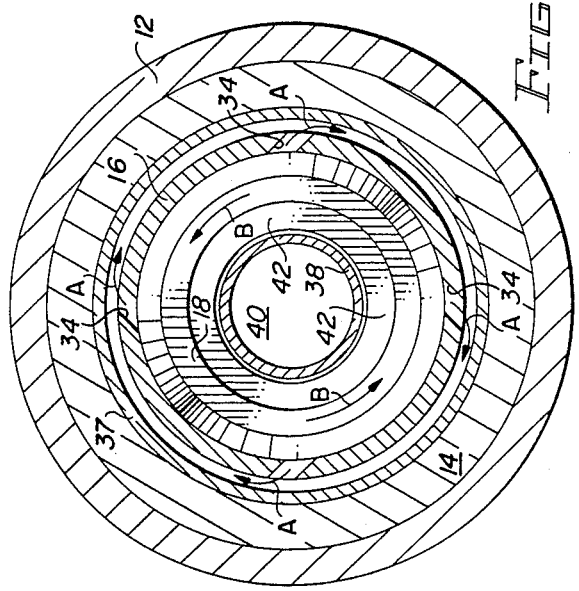
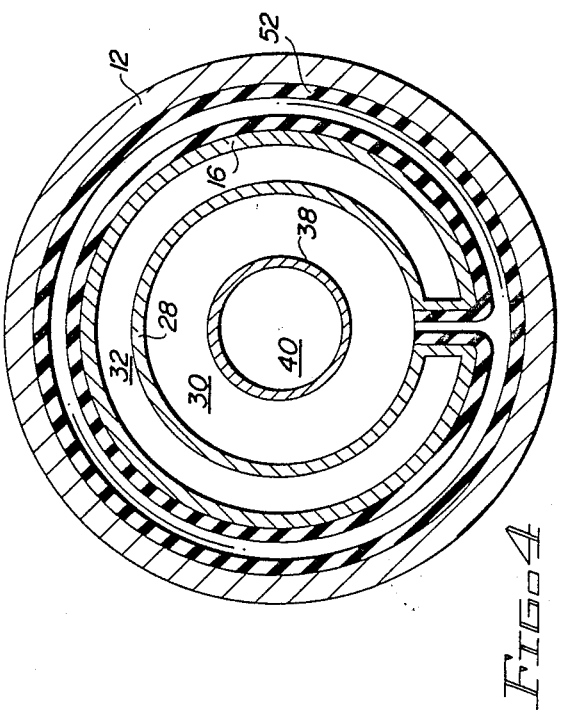

HYDRO-ROTARY VASCULAR CATHETER

CROSS-REFERENCE TO RELATED APPLICATION

This application is a continuation-in-part of my earlier application entitled "Hydro-Rotary Vascular Catheter" which was filed on July 7, 1988 and assigned Ser. No. 216,095, now abandoned.

BACKGROUND OF THE INVENTION

1. Field of the Invention

This invention relates in general to catheters for removing obstructions from vessels carrying body fluids and, more particularly, to a hydro-rotary vascular catheter for removing plaque from blood vessels.

2. Description of the Prior Art

The removal of harmful blockages from ducts and passages within the body is typically accomplished by one of two conventional techniques. The first technique, called balloon angioplasty, utilizes a treatment catheter equipped with two inflatable balloons which seal off a constricted area in a duct or passage such as a blood vessel. An inlet member is provided within the catheter for supplying a suitable solvent, such as a solution of digestive enzymes, to the area delimited by the two balloons, and an outlet member is provided for removing the dissolved material from the area. In addition, a second supply channel is provided for allowing the blood or other body fluid to bypass the delimited area, thus preventing a complete coronary obstruction. Representative examples of this type of catheter are found in U.S. Pat. No. 4,423,725 to Baran et al, U.S. Pat. No. 4,445,892 to Hussein et al, and U.S. Pat. Nos. 4,573,966 and 4,610,662 to Weikl et al.

A major problem with the above type of catheter is that the solvent used to remove the obstruction may attack the walls of the blood vessel itself as well as the harmful substances it is intended to dissolve. This can lead to perforation or rupturing of the blood vessel, which can endanger the life of the patient.

The problems associated with balloon angioplasty have led to the development of a second technique, known as laser angioplasty, which uses laser energy rather than a chemical solvent to vaporize the obstruction. A typical example of a laser angioplasty catheter is described in U.S. Pat. No. 4,685,458 to Leckrone. In Leckrone, the catheter, which is mounted for rotation and translation about a filament, has a pair of abutments disposed on its distal end. Also included on the distal end of the catheter is a bladder which, when inflated, causes the abutments to bear against the inner surface of the blood vessel so that the space between the abutments defines a working chamber for delimiting the area around an obstruction. A fiber optic connected to a source of laser energy extends through the catheter, with the distal end of the fiber optic being disposed in one of the abutments. In addition, a suction port is provided between the abutments for removing disintegrated material from the delimited area. Severing means such as a blade or heated element may also be included for severing and releasing material which is not vaporized by the laser.

Like balloon angioplasty, however, laser angioplasty can result in perforation or rupture of the blood vessel itself unless great care is taken to control the intensity and level of the laser energy as well as the direction in which the energy is emitted.

In response to the above problems, a third type of catheter has been introduced. This catheter, disclosed in U.S. Pat. No. 4,631,052 to Kensey, comprises a bladed cutting head which is rotated by turbine drive to cut away occlusions in a body vessel. However, this catheter poses a potential danger to the patient if the rotary head should happen to bounce off an especially hard portion of an occlusion and cut through a vessel wall.

Accordingly, there exists a need for a new and improved vascular catheter which overcomes the shortcomings of the prior art.

SUMMARY OF THE INVENTION

The catheter of the present invention comprises a tubular outer shell having a non-abrasive rotary fluid-directing head rotatably mounted at its distal end. A plurality of flow-directing outlet passages, or nozzles, are arranged in rows about the circumference of the head. A protective shield surrounds the row of outlet passages nearest the base of the rotary head.

An inner wall divides the interior of the outer shell into two coaxial conduits, with the inner conduit defining a supply channel for conducting a relatively highly pressurized flushing fluid into the constricted area of a vessel containing body fluid, and the outer conduit defining a return channel for carrying debris away from the constricted area. A hollow needle is mounted for axial movement within the supply channel. The interior of the hollow needle defines a blood supply duct for supplying the patient's blood under pressure to a location downstream of the constricted area. A first balloon is carried at the distal end of the needle, and a second balloon is carried peripherally about the outer shell of the catheter, upstream of the first balloon. Both balloons are expandable so as to contact the inside walls of said vessel to operatively seal off and isolate the constricted area.

Treatment of a constricted vessel is as follows. First, the catheter is inserted in the vessel and advanced until the rotary head reaches the constricted area. Then the needle is pushed forwardly in the catheter until its distal end extends beyond the obstruction. The patient's blood is then supplied under pressure to the needle, causing the first balloon to inflate and seal off the downstream end of the constricted area. Complete occlusion of the vessel is avoided however, because a small outlet provided in the first balloon allows the pressurized blood to reenter the vessel downstream of the obstruction.

After the first balloon has been inflated, a pressurized flushing fluid such as saline solution, digestive enzyme or other available solvent, is applied to the supply channel of the catheter. A portion of the flushing fluid is diverted into the second balloon, causing the second balloon to inflate and seal off the upstream end of the constricted area. The remaining flushing fluid is ejected at a high velocity through the outlet passages in the rotary head, causing the head to rotate about its longitudinal axis. The force of the streams of relatively high-pressure flushing fluid ejected by the fluid-directing rotating head is sufficient to mechanically break down all or most of the blockage in the vessel. The streams of fluid from the nozzles nearest the base of the head, which are directed outwardly substantially in a plane perpendicular to the axis of rotation of the head, are prevented from directly impacting and possibly rupturing the walls of the blood vessels by the protective shield, which diverts the fluid in a forward, rather than radial, direction. This flow, plus the flow from the forwardly nozzles in the forward portion of the head, creates turbulent flow in the space between the rotating head and the blockage to be removed.

A lower pressure in the return channel of the catheter then enables the debris from the blockage released by the turbulent flow of the fluid to flow out of the constricted area via the openings in the outer shell of the catheter and through a filtering system where a physician can observe and analyze the characteristics of the removed material.

Because the catheter of the present invention relies on the mechanical action of the fluid exiting the rotary fluid-directing head rather than on the chemical action of a solvent, the cutting action of a bladed head, or the thermal energy of a laser, the risk of abrasion or other damage to the walls of the vessel is minimized in most circumstances. However, in cases where the occlusion is so severe that the needle can not initially fit through, a laser fiber optic may be inserted through the center of the catheter and used to burn a large enough hole in the occlusion to accommodate the needle.

Accordingly, it is an object of this invention to provide a new and useful vascular catheter with a pressurized fluid-directing rotary head for breaking down plaque and other harmful accumulations in a body vessel such as an artery, primarily by means of the action of the turbulent flow of the fluid exiting the rotating head.

Another object of the invention is to provide a vascular catheter with a rotary fluid-directing head in which the pressurized fluid flowing through the nozzles of the head is the source of energy for imparting a spin to the rotary head.

Another object of the invention is to provide a hydro-rotary vascular catheter with a return channel which enables debris to be removed from the obstructed area simultaneously with the break-down process, while the catheter is in place in the body vessel.

Still another object of the invention is to provide a hydro-rotary vascular catheter with means for isolating a constricted area of a vessel without cutting off the supply of body fluid (such as blood) to areas downstream of the constriction.

Yet still another object of the invention is to provide a hydro-rotary vascular catheter with a protective shield which prevents the walls of a body vessel from being damaged by fluid ejected radially through the fluid-directing rotary head.

The foregoing and other objects of the present invention, as well as the invention itself, may be more fully understood from the following description when read in conjunction with the accompanying drawings.

BRIEF DESCRIPTION OF THE DRAWINGS

FIG. 1 is a fragmentary perspective view showing the vascular catheter of the present invention.

FIG. 2 is a sectional view taken through line 2—2 of FIG. 1, showing the catheter in a pre-activated mode in a blood vessel.

FIG. 3 is a sectional view similar to FIG. 2, showing the catheter in an activated mode in the vessel.

FIG. 4 is a sectional view taken through line 4—4 of FIG. 3.

FIG. 5 is a sectional view taken through line 5—5 of FIG. 3.

DESCRIPTION OF THE PREFERRED EMBODIMENT

Referring more particularly to the drawings, FIG. 1 shows the distal end of the rotary catheter of the present invention, indicated in its entirety by the numeral 10. FIGS. 2 and 3 show the distal end of the catheter 10 after insertion into a vessel 12 of a patient. The proximal end of the catheter 10, not shown, remains external to the body of the patient where it can be easily observed and manipulated by the surgeon and/or medical technicians. By way of example, the vessel 12 will be referred to in the following paragraphs as a "blood vessel." However, the principles embodied in the invention need not be limited to use in blood vessels, but can be applied equally effectively to a trachea, bladder, urethra, or any other body passage which is blocked by undesired material such as calcified and fatty tissue 14.

The catheter 10 comprises a tubular outer shell 16 having a non-abrasive head 18 rotatably mounted on its distal end. A central opening 19 is formed at the distal end of the head 18. Both the outer shell 16 and the head 18 are preferably made from, or coated with, a noncorrosive synthetic resin material such as "Teflon" which prevents adhesion of the undesired material 14 to the catheter 10, and is sterile, easy to clean, and biocompatible with the patient's blood.

The head 18 is connected to the shell 16 by means of an integrally formed keeper ring 22 at the distal end of the catheter 10. The keeper ring 22 includes an inwardly extending rim 24, which engages a groove 26 formed along the inside of the base of the head 18. Both the rim 24 of the keeper ring 22 and the lower edge 27 of the head 18 are beveled to allow the head 18 to be easily snapped on the shell 16, but preventing removal of the head 18 once it has been snapped into place. Thus, there is little or no possibility of the head 18 accidentally becoming detached from the outer shell 16 while in the patient's blood vessel 16.

An annular inner wall 28 divides the interior of the shell 16 into two coaxial conduits, with the inner conduit 30 defining a supply channel and the outer conduit 32 defining a return channel which preferably opens to the atmosphere at its proximal end. The inner conduit 30 communicates with the interior of the blood vessel 12 by means of a plurality of outlet passages formed along the circumference of the head 18. The outer flow conduit 32 communicates with the interior of the blood vessel 12 by means of at least one opening 33 extending through the outer shell 16.

The outlet passages, or nozzles, in the rotary fluid-directing head 18 are arranged in a plurality of rows, including a row of primary passages or nozzles 34 formed along the base of the rotary fluid-directing head 18, and at least one row of secondary passages 35 formed nearer the forward end of the rotary fluid-directing head 18. The longitudinal axis of each of the primary outlet passages 34 is oriented with respect to axis 36 so that the velocity of fluid exiting the passages 34 will produces a torque causing the rotary fluid-directing head 18 to spin, or to rotate, around axis 36. It should be noted that spin axis 36 is also the longitudinal axis of shell 16. Each each of the secondary outlet passages 35 is also oriented with respect to axis 36 to eject the fluid in a primarily forward direction, or more forwardly direction. However, than passage 34 the secondary outlet passages will also have a produce additional torgue which aids in rotating head 18, or in causing head 18 to spin around its spin axis 36. The primary outlet passages 34 are surrounded by a protective shield 37 which extends forwardly and circumferentially from the forward end of tubular body 16, thus preventing high-pressure fluid exiting passages 34 from directly striking the vessel 12 and possibly rupturing the walls thereof.

A hollow needle 38 is mounted for axial movement within the inner conduit or supply channel 30, with the interior 40 of the needle 38 defining a blood supply duct. Lateral movement of the needle 38 within the channel 30 is limited by means of a tubular guide member 42 which extends proximally from the central opening 19 in the head 18. Note that, with the exception of the tubular guide member 42, the inner conduit or supply channel 30 is free of obstructions. This makes it possible to easily remove the needle 38 from the conduit 30 if necessary, and to insert another device such as a laser transmitting fiber optic (not shown) inside the catheter 10. Such a fiber might, for instance, be part of an optical system used to view the constricted area, or in situations where the blockage is so severe that the mechanical action of the rotary fluid-directing head 18 can not be used to break down the obstruction, it might be used to "loosen up" the calcified and fatty tissue 14 in the vessel prior to activating the rotary head 18.

A first expandable balloon 48, the thickness of which has been exaggerated for illustrative puroposes, is carried at the distal end of the needle 38, with a small aperture 50 being provided in the balloon 48 to allow the patient's blood to reenter the vessel 12 downstream of the calcified tissue 14. A second expandable balloon 52 (thickness again exaggerated) is carried peripherally about the outer shell 16 of the catheter 10, upstream of the first balloon 48. The mouth of the second balloon 52 is mounted in a small, radially extending passageway 54 which communicates with the supply channel 30.

OPERATION

Treatment of a constricted vessel is as follows. First, the catheter 10 is inserted in the vessel 12 and advanced until the rotary fluid-directing head 18 reaches the constricted area. Then the needle 38 is pushed forwardly in the catheter 10 until its distal end extends through the central opening 19 in the rotary fluid-directing head 18 and beyond the obstruction 14. The patient's blood is then supplied under pressure to the needle 38, causing the first balloon 48 to inflate and seal off the downstream end of the constricted area, as shown in FIG. 3. Complete occlusion of the vessel 12 is avoided however, because the small outlet 50 provided in the first balloon 48 allows the pressurized blood to reenter the vessel 12 downstream of the obstruction 14. The pressure at which the patient's blood is pumped through the needle 38 must be considerably higher than the patient's normal blood pressure in order to compensate for pressure drops within the blood vessel 12 downstream of the distal balloon 48.

After the upstream end of the constricted area is sealed off by the first balloon 48, a pressurized flushing fluid, which is preferably a mild, chemically neutral liquid such as saline solution or distilled water, is applied to the supply channel 30 of the catheter. A portion of the flushing fluid flows into the second balloon 52 via the radially extending passageway 54, causing the second balloon 52 to inflate and seal off the upstream end of the constricted area. The remaining pressurized fluid is ejected at a relatively high velocity through the outlet passages 34, 35 in the rotary fluid-directing head 18, as shown by the arrows A in FIG. 5. This in turn causes the head 18 to rotate about its spin axis 36 in the direction of arrows B. In addition, a portion of the exiting fluid will strike protective shield 37, thus inducing turbulent flow, as indicated by arrows C. The force of the turbulent, high pressure streams of fluid emitted by the rotary fluid-directing head is usually sufficient to break down the plaque and other obstruction material 14 in the vessel 12. Lower pressure in the return channel 32 of the catheter 10 then causes the debris from the blockage 14 to flow out of the constricted area via the openings 33 in the outer shell 16 of the catheter 10. A conventional filtering mechanism may be provided at the outlet of the return channel to enable a physician to monitor the plaque and the like as it exits the patient's body.

As noted earlier, the mechanical action of the fluid ejected through the fluid-directing head 18 is usually sufficient to cut through the calcified and fatty tissue 14 obstructing the blood vessel 12. This, in most cases, enables the use of a mild flushing fluid rather than powerful chemical solvent which could damage the inner wall of the vessel 12. In extreme cases, however, it may be desirable to use a more powerful substance such as a solution of digestive enzymes or the like.

While the principles of the invention have now been made clear in the illustrated embodiments, there will be immediately obvious to those skilled in the art, many modifications of structure, arrangements, proportions, the elements, materials and components used in the practice of the invention and otherwise, which are particularly adapted for specific environments and operation requirements without departing from those principles.

What I claim is:

1. A catheter apparatus for removing undesired material from a constricted area in a vessel of a patient containing a body fluid, said apparatus comprising:
   (a) a tubular shell for insertion within the vessel in the patient's body, said shell having a proximal end, a distal end, and a longitudinal axis;
   (b) a non-abrasive rotary fluid-directing head secured to the distal end of said outer shell and mounted for rotation about the longitudinal axis of said shell;
   (c) isolation means for isolating said constricted area from the rest of said vessel, said isolation means including (i) first isolation means mounted on said shell for placement upstream of said constricted area, and (ii) second isolation means mounted in the distal end of said shell for placement downstream of said constricted area;
   (d) first supply means in said tubular shell for introducing a flushing fluid into said constricted area at a relatively high pressure;
   (e) second supply means in said tubular shell for carrying the body fluid beyond said second isolation means to allow circulation of the body fluid downstream of said constricted area;
   (f) spin means for imparting a spin to said rotary fluid-directing head, said spin means including primary outlet passages formed through said rotary fluid-directing head for directing streams of pressurized flushing fluid exiting said outlet passages to produce a torque causing said head to spin around the longitudinal axis of said shell;
   (g) return means in said shell for carrying flushing fluid and debris created by action of said catheter apparatus away from the constricted area in said vessel out of the patient's body; and (h) shield means for preventing fluid exiting said primary outlet passages from directly impacting said vessel.

2. The catheter apparatus of claim 1, in which said isolation means comprises two balloon means, including a first balloon means for placement downstream of the constricted area and a second balloon means for placement upstream of the constricted area, each of said balloon means being expandable by a pressure medium so as to contact the inside walls of said vessel to operatively seal off and isolate the constricted area.

3. The catheter apparatus of claim 1, in which said rotary fluid-directing head further comprises secondary openings formed forwardly of said primary openings, each of said secondary openings communicating at one end with said first supply means and being oriented to eject fluid in primarily forward direction.

4. A catheter apparatus for removing undesired material from a constricted area in a vessel containing a body fluid, said apparatus comprising:
   (a) a tubular outer shell for insertion in a vessel within a patient's body, said shell having a proximal end and a distal end;
   (b) a nonabrasive rotary fluid-directing head mounted on the distal end of said outer shell for rotation about a spin axis;
   (c) two balloon means, including a first balloon means for placement downstream of the constricted area and a second balloon means for placement upstream of the constricted area, each of said balloon means being expandable by a pressurized medium to contact the inside walls of said vessel to operatively seal off and isolate the constricted area;
   (d) a flushing fluid supply conduit disposed within said outer shell for delivering a pressurized flushing fluid to the constricted area;
   (e) a body fluid supply duct disposed within said outer shell for delivering said patients body fluid under pressure to a location downstream of the constricted area and beyond said first balloon means;
   (f) spin means for imparting a spin to said rotary fluid-directing head, said spin means including primary outlet passages formed through said rotary fluid-directing head, each of said outlet passages communicating with said flushing fluid supply conduit and being oriented to cause flushing fluid exiting said primary outlet passages to produce a torque causing said head to spin around its spin axis;
   (g) a return conduit for carrying flushing fluid and debris from said undesired material from the constricted area created by the action of the flushing fluid exiting said rotary fluid-directing head away from said constricted area and out of the patient's body; and
   (h) shield means mounted on the tubular shell for preventing fluid exiting said primary outlet passages from directly impacting said vessel.

5. The catheter apparatus of claim 4, in which said body fluid supply duct comprises a hollow needle disposed for axial movement within said tubular outer shell, said first balloon means being carried in the distal end of said needle and being in fluid communication with the interior of said needle so as to be inflated by the pressurized body fluid carried within said needle.

6. The catheter apparatus of claim 5, in which said first balloon means defines an aperture for allowing the patient's body fluid to exit the catheter and reenter the vessel downstream of the constricted area.

7. The catheter apparatus of claim 4, in which said second balloon means is carried peripherally about said tubular outer shell of said catheter, said second balloon being in fluid communication with a radially extending passageway leading from said supply channel for allowing the pressurized flushing fluid in said supply channel to enter and inflate said second balloon.

8. The catheter apparatus of claim 4, in which said rotary fluid-directing head further comprises secondary openings formed forwardly of said primary openings, each of said secondary openings communicating at one end with said first supply means and being oriented to eject fluid in a primarily forward direction.

9. A vascular catheter apparatus for removing undesired material from a constricted area in a blood vessel of a patient, said apparatus comprising:
   (a) a tubular outer shell for insertion within the blood vessel, said shell having a proximal end and a distal end;
   (b) an annular inner wall dividing the interior of said tubular outer shell into two coaxial conduits, the inner conduit defining a supply channel for transporting a pressurized flushing fluid to the distal end of the outer shell and the outer conduit comprising a return channel communicating with at least one opening in said tubular outer shell for allowing fluids and undesired material in the blood vessel to enter said return channel for removal from the patient;
   (c) a nonabrasive rotary fluid-directing head mounted on the distal end of said outer shell for rotation about an axis of rotation, said head being in communication with the supply channel of the shell, a central opening formed at the distal end of said rotary fluid-directing head, and a plurality of primary outlet passages formed through a circumference of said rotary fluid-directing head, each of said primary outlet passages being oriented with respect to the axis of rotation of said head so that pressurized flushing fluid from the supply channel exiting said primary outlet passages produces a torque acting to rotate said head about its axis of rotation;
   (d) a hollow needle defining a blood supply duct for conducting the patients's blood under pressure through the constricted area, said hollow needle being disposed for axial movement in said supply channel from a retracted position totally within said outer shell to an extended position in which the distal end of said needle protrudes through said central opening in the distal end of said rotary fluid-directing head and beyond the constricted area of the vessel;
   (e) a first inflatable balloon carried in the distal end of said hollow needle, said first inflatable balloon being in fluid communication with the interior of said hollow needle and being expandable by the pressurized blood to contact the inside walls of said vessel to operatively seal of and isolate the downstream end of said constricted area, said first balloon having an aperture for allowing blood to enter the patients blood vessel downstream of the constricted area;

(f) a second inflatable balloon carried peripherally about said tubular outer shell of said catheter at a location upstream of said first inflatable balloon, said second balloon being in fluid communication with a radially extending passageway leading from the supply channel to allow pressurized flushing fluid from said supply channel to enter and to inflate the second balloon causing the second balloon to contact the inside walls of the blood vessel to operatively seal off and to isolate the upstream end of the constricted area; and (g) protective shield means mounted on the distal end of the shield surrounding and spaced from that portion of said head through which the primary outlet passages passages are formed for preventing pressurized flushing fluid exiting said primary outlet passages from directly impacting said vessel;

whereby, after blood has been supplied under pressure to said blood supply duct in said hollow needle and a pressurized flushing fluid has been supplied to the supply channel, causing the first and second balloons to inflate and seal off the constricted area, the pressurized flushing fluid exiting through the primary outlet passages of said head cause said head to rotate about its spin axis, the rotation of the head and the turbulent flow of the flushing fluid in the isolated restricted area removing undesired material from the restricted area of the vessel which flushing fluid and removed undesired material enters the catheter through said opening in the tubular outer shell for removal from the patient's body.

10. The vascular catheter apparatus of claim 9, in which said pressurized flushing fluid comprises a saline solution.

11. The vascular catheter apparatus of claim 9, in which said pressurized flushing fluid comprises a solution of digestive enzymes.

12. The catheter apparatus of claim 9, in which said head further comprises at least one row of secondary openings formed forwardly of said primary openings, each of said secondary openings communicating at one end with said first supply means and being oriented to eject fluid in a primarily forward direction.

* * * * *